United States Patent [19]

Rutter et al.

[11] Patent Number: 4,652,525

[45] Date of Patent: Mar. 24, 1987

[54] RECOMBINANT BACTERIAL PLASMIDS CONTAINING THE CODING SEQUENCES OF INSULIN GENES

[75] Inventors: William J. Rutter; Raymond Pictet; John Chirgwin; Howard M. Goodman; Axel Ullrich; John Shine, all of San Francisco, Calif.

[73] Assignee: The Regents of the University of California, Berkeley, Calif.

[21] Appl. No.: 508,651

[22] Filed: Jun. 28, 1983

Related U.S. Application Data

[63] Continuation of Ser. No. 897,709, Apr. 19, 1978, abandoned, which is a continuation-in-part of Ser. No. 801,343, May 27, 1977, abandoned, and a continuation-in-part of Ser. No. 805,023, Jun. 9, 1977, abandoned.

[51] Int. Cl.$^4$ .................... C12N 1/20; C12N 1/00; C12N 15/00; C12R 1/19

[52] U.S. Cl. .................... 435/253; 435/317; 435/172.3; 435/849

[58] Field of Search .............. 435/172.3, 68, 70, 71, 435/253, 317

[56] References Cited

U.S. PATENT DOCUMENTS 4,440,859  4/1984  Rutter et al. .................... 435/68

OTHER PUBLICATIONS

Wood et al, Nucleic Acids Research, vol. 3, pp. 1961–1971, Aug. 1976.
Higuchi et al, PNAS USA, vol. 73, pp. 3146–3150, Sep. 1976.
Rougeon et al, Nucleic Acids Research, vol. 2, pp. 2365–2378.
Chan et al, PNAS, vol. 73, pp. 1964–1968, Jun. 1976.

Primary Examiner—Alvin E. Tanenholtz
Attorney, Agent, or Firm—Ciotti & Murashige

[57] ABSTRACT

A recombinant procaryotic microorganism containing the gene coding for insulin.

7 Claims, No Drawings

RECOMBINANT BACTERIAL PLASMIDS CONTAINING THE CODING SEQUENCES OF INSULIN GENES

The Government has rights in this invention pursuant to Grants No. GM-21830 and CA 14026 awarded by the Department of Health, Education and Welfare.

This is a continuation of application Ser. No. 897,709 filed Apr. 19, 1978, abandoned which is a continuation in part of Ser. No. 801,343 filed May 27, 1977, abandoned and a continuation in part of 805,023 filed June 9, 1977, abandoned.

BACKGROUND OF THE INVENTION

The present invention relates to the isolation of a specific nucleotide sequence which contains the genetic information coding for a specific protein, the synthesis of DNA having this specific nucleotide sequence and transfer of that DNA to a microorganism host wherein the DNA may be replicated. More specifically, the present invention relates to the isolation of the insulin gene, its purification, transfer and replication in a microbial host and its subsequent characterization. Novel products are produced according to the present invention. These products include a recombinant plasmid containing the specific nucleotide sequences derived from a higher organism and a novel microorganism containing as part of its genetic makeup a specific nucleotide sequence derived from a higher organism.

The symbols and abbreviations used herein are set forth in the following table:
DNA—deoxyribonucleic acid
RNA—ribonucleic acid
cDNA—complementary DNA (enzymatically synthesized from an mRNA sequence)
mRNA—messenger RNA
tRNA—transfer RNA
dATP—deoxyadenosine triphosphate
dGTP—deoxyguanosine triphosphate
dCTP—deoxycytidine triphosphate
A—Adenine
T—Thymine
G—Guanine
C—Cytosine
Tris-2-Amino-2-hydroxyethyl-1,3-propanediol
EDTA—ethylenediamine tetraacetic acid
ATP—adenosine triphosphate
TTP—thymidine triphosphate DNA is a high molecular weight polymer of biological origin. The structural units of the polymer are deoxyribonucleotides, each of which contains a purine or pyrimidine base to which is linked deoxyribose having a phosphate moiety esterified at the 3' or 5' hydroxyl of the deoxyribose. The polymer is constructed by the linking together of deoxyribonucleotides by the formation of phosphodiester bonds between the 5' position of one nucleotide and the 3' of its next neighbor. A linear polymer of nucleotides is thus formed, sometimes having at one terminus a free 5' phosphate and/or at the other a free 3' phosphate. In some instances one or both of the phosphate termini may be removed by hydrolysis leaving free 5' or 3' hydroxyl ends. The significant feature of this linkage mode is that it results in a polynucleotide strand which is directional in the sense that one end can be distinguished from the other.

There are four purine or pyrimidine bases found in the vast majority of DNA's which have been analyzed. These are the purines, adenine and guanine, and the pyrimidines, cytosine and thymine (hereinafter A, G, C, and T, respectively). It is the specific sequence of the bases A, G, C, and T which confers the biological functions of DNA as the repository of genetic information in a living cell.

The native conformation of DNA is in the form of paired polynucleotide strands of opposite directionality. The strands are held together by the cooperative effect of multiple hydrogen bonding between specific purine-pyrimidine pairs. The molecular sizes and hydrogen bonding angles are such that A and T form a specific pair and G and C form a specific pair. As a result, the base sequence in one strand of native DNA is mirrored by a complementary sequence in the other strand, due to the base pairing relationships just described. By way of illustrating this relationship, a heptanucleotide having the sequence ACCGTTG, reading from the 5' end to the 3' end, will be found paired with a complementary strand having the sequence CAACGGT from 5' to 3'. By convention, however, the native structure is depicted with one strand in the 5' to 3' orientation and the complementary strand in the 3' to 5' orientation:

5' ACCGTTG 3'

3' TGGCAAC 5'

DNA may exist in several alternate states in addition to the native configuration, a linear double stranded polymer, as described above. It may also exist as individual single strands and it may exist as a double stranded molecule for a portion of its length but containing single stranded gaps or single stranded ends. Of particular biological significance is the fact that DNA commonly forms closed rings by the formation of phosphodiester bonds between its opposite ends. The 5' end of one strand joins its 3' end by means of a phosphodiester linkage, and a similar linkage is formed between the 5' and 3' ends of the complementary strand. Such rings have been found ranging in molecular weight from less than $1 \times 10^6$ to more than $1 \times 10^9$. Rings which are not covalently closed can also be formed. A procedure for forming such rings from double stranded linear DNA has been developed in the prior art and will be described in detail below. In general, the procedure involves the addition of complementary sequences to either the 5' or 3' ends of the linear molecule. Such complementary single strand sequences are termed cohesive ends because they are capable of pairing with each other by means of the specific hydrogen bonded base pairing relationships described. When such pairing occurs, under the appropriate conditions of temperature, ionic strength and solvent composition, a double stranded ring can be formed, held in place by the hydrogen bonding interactions of the cohesive ends. Similarly a small linear piece may be joined with a large linear piece provided the two have cohesive ends of complementary sequence, and the combination can also form a closed ring if both ends of both molecules are mutually cohesive. Enzyme reactions can form covalent bonds joining the ends and stabilizing the structure.

The biological significance of the base sequence of DNA, as previously stated, is as a repository of genetic information. It is known that the sequence of bases in DNA is used as a code specifying the amino acid sequence of all proteins made by the cell. In addition, portions of the sequence are used for regulatory purposes, to control the timing and amount of each protein made. The nature of these controlling elements is only partially understood. Finally, the sequence of bases in each strand is used as a template for the replication of DNA which accompanies cell division.

The manner by which base sequence information in DNA is used to determine the amino acid sequence of proteins is a fundamental process which, in its broad outlines is universal to all living organisms. It has been shown that each amino acid commonly found in proteins is determined by one or more trinucleotide or triplet sequences. Therefore, for each protein, there is a corresponding segment of DNA containing a sequence of triplets corresponding to the protein amino acid sequence. The genetic code is shown in the accompanying table.

In the process of converting the nucleotide sequence information into amino acid sequence structure, a first step, termed transcription, is carried out. In this step, a local segment of DNA having a sequence which specifies the protein to be made is first copied with RNA. RNA is a polynucleotide similar to DNA except that ribose is substituted for deoxyribose and uracil is used in place of thymine. The bases in RNA are capable of entering into the same kind of base pairing relationships that exist with DNA. Consequently, the RNA transcript of a DNA nucleotide sequence will be complementary to the sequence copied. Such RNA is termed messenger RNA (mRNA) because of its status as an intermediary between the genetic apparatus and the protein synthesizing apparatus of the cell. Isolation of intact mRNA is technically extremely difficult due to the presence of the enzyme RNase which catalyzes the hydrolysis of the phosphodiester bonds in the ribonucleotide sequence. This enzyme is ubiquitous, extremely stable and highly active. The hydrolysis of a single phosphodiester bond within the mRNA chain cannot be tolerated since that would destroy the sequence continuity necessary to preserve the genetic information. Within the cell, mRNA is used as a template in a complex process involving a multiplicity of enzymes and organelles within the cell, which results in the synthesis of the specified amino acid sequence. This process is referred to as the translation of the mRNA.

There are often additional steps, called processing, which are carried out to convert the amino acid sequence synthesized by the translational process into a functional protein. An example is provided in the case of insulin.

| Genetic Code | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter triplet represents a trinucleotide of mRNA, having a 5' end on the left and a 3' end on the right. The letters stand for the purine or pyrimidine bases forming the nucleotide sequence.
A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T
QR=AG is S if T or C
S=A, G, C or T if QR is TC
S=T or C if QR is AG
J=A or G
K=T or C
L=A, T, C or G
M=A, C or T The immediate precursor of insulin is a single polypeptide, termed proinsulin, which contains the two insulin chains A and B connected by another peptide, C. See Steiner, D. F., Cunningham, D., Spigelman, L. and Aten, B., *Science* 157, 697 (1967). Recently it has been reported that the initial translation product of insulin mRNA is not proinsulin itself, but a preproinsulin that contains more than 20 additional amino acids on the amino terminus of proinsulin, See Cahn, S. J., Keim, P. and Steiner, D. F., *Proc. Natl. Acad. Sci. USA* 73, 1964 (1976) and Lomedico, P. T. and Saunders, G. F., *Nucl. Acids Res.* 3, 381 (1976). The structure of the preproinsulin molecule can be represented schematically as NH$_2$-(pre-peptide)-B chain-(C peptide)-A chain-COOH.

Many proteins of medical or research significance are found in or made by the cells of higher organisms such as vertebrates. These include, for example, the hormone insulin, other peptide hormones such as growth hormone, proteins involved in the regulation of blood pressure, and a variety of enzymes having industrial, medical or research significance. It is frequently difficult to obtain such proteins in usable quantities by extraction from the organism, and this problem is especially acute in the case of proteins of human origin. Therefore there is a need for techinques whereby such proteins can be made by cells outside the organism in reasonable quantity. In certain instances, it is possible to obtain appropriate cell lines which can be maintained by the techniques of tissue culture. However, the growth of cells in tissue culture is slow, the medium is expensive, conditions must be accurately controlled, and yields are low. Moreover, it is often difficult to maintain a cultured cell line having the desired differentiated characteristics.

In contrast, microorganisms such as bacteria are relatively easy to grow in chemically defined media. Fermentation technology is highly advanced, and can be well controlled. Growth of organisms is rapid and high yields are possible. In addition, certain microorganisms have been thoroughly characterized genetically and in fact are among the best characterized and best understood organisms.

Therefore it is highly desirable to achieve the transfer of a gene coding for a protein of medical significance, from an organism which normally makes the protein to an appropriate microorganism. In this way it is possible that the protein could eventually be made by the microorganism, under controlled conditions of growth, and obtained in the desired quantities. It is also possible that substantial reductions in the over-all costs of producing the desired protein could be achieved by such a process. In addition, the ability to isolate and transfer the genetic sequence which determines the production of a particular protein into a microorganism having a well-defined genetic background could provide a research tool of great value to the study of how the synthesis of such a protein is controlled and how the protein is processed after synthesis.

The present invention provides a means for achieving the above recited goals. A process is disclosed involving a complex series of steps involving enzyme-catalyzed reactions. The nature of these enzyme reactions as they are understood in the prior art is described herewith.

Reverse transcriptase catalyzes the synthesis of DNA complementary to an RNA template strand in the presence of the RNA template, an oligodeoxynucleotide primer and the four deoxynucleoside triphosphates, dATP, dGTP, dCTP, and TTP. The reaction is initiated by the non-covalent bonding of the oligo-deoxynucleotide primer to the 3' end of mRNA followed by stepwise addition of the appropriate deoxynucleotides, as determined by base pairing relationships with the mRNA nucleotide sequence, to the 3' end of the growing chain. The product molecule may be described as a hairpin structure containing the original RNA together with a complementary strand of DNA joined to it by a single stranded loop of DNA. Reverse transcriptase is also capable of catalyzing a similar reaction using a single stranded DNA template, in which case the resulting product is a double stranded DNA hairpin having a loop of single stranded DNA joining one set of ends. See Aviv, H. and Leder, P., *Proc. Natl. Acad. Sci. USA* 69, 1408 (1972) and Efstratiadis, A., Kafatos, F. C., Maxam, A. F. and Maniatis, T., *Cell* 7, 279 (1976).

Restriction endonucleases are enzymes capable of hydrolyzing phosphodiester bonds in double stranded DNA, thereby creating a break in the continuity of the DNA strand. If the DNA is in the form of a closed loop, the loop is converted to a linear structure. The principal feature of an enzyme of this type is that its hydrolytic action is exerted only at a point where a specific nucleotide sequence occurs. Such a sequence is termed the recognition site for the restriction endonuclease. Restriction endonucleases from a variety of sources have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Since any DNA susceptible of cleavage by such an enzyme must contain the same recognition site, the same cohesive ends will be produced, so that it is possible to join heterologous sequences of DNA which have been treated with restriction endonuclease to other sequences similarly treated. See Roberts, R. J., *Crit. Rev. Biochem* 4, 123 (1976). Restriction sites are relatively rare, however the general utility of restriction endonucleases has been greatly amplified by the chemical synthesis of double stranded oligonucleotides bearing the restriction site sequence. Therefore virtually any segment of DNA can be coupled to any other segment simply by attaching the appropriate restriction oligonucleotide to the ends of the molecule, and subjecting the product to the hydrolytic action of the appropriate restriction endonuclease, thereby producing the requisite cohesive ends. See Heyneker, H. L., Shine, J., Goodman, H. M., Boyer, H. W., Rosenberg, J., Dickerson, R. E., Narang, S. A., Itakura, K., Lin, S. and Riggs, A. D., *Nature* 263, 748 (1976) and Scheller, R. H., Dickerson, R. E., Boyer, H. W., Riggs, A. D. and Itakura, K., *Science* 196, 177 (1977).

S1 endonuclease is an enzyme of general specificity capable of hydrolyzing the phosphodiester bonds of single stranded DNA or of single stranded gaps or loops in otherwise double stranded DNA. See Vogt, V. M., *Eur. J. Biochem*, 33, 192 (1973).

DNA ligase is an enzyme capable of catalyzing the formation of a phosphodiester bond between two segments of DNA having a 5' phosphate and a 3' hydroxyl, respectively, such as might by formed by two DNA fragments held together by means of cohesive ends. The normal function of the enzyme is thought to be in the joining of single strand nicks in an otherwise double stranded DNA molecule. However, under appropriate conditions, DNA ligase is capable of catalyzing blunt end ligation in which two molecules having blunt ends are covalently joined. See Sgaramella, V., Van de Sande, J. H., and Khorana, H. G., *Proc. Natl. Acad. Sci. USA* 67, 1468 (1970).

Alkaline phosphatase is an enzyme of general specificity capable of hydrolyzing phosphate esters including 5' terminal phosphates on DNA.

A further step in the overall process to be described is the insertion of a specific DNA fragment into a DNA vector, such as a plasmid. Plasmid is the term applied to any autonomously replicating DNA unit which might be found in a microbial cell, other than the genome of the host cell itself. A plasmid is not genetically linked to the chromosome of the host cell. Plasmid DNA's exist as double stranded ring molecules generally on the order of a few million molecular weight, although some are greater than 10% molecular weight, and they unually represent only a small percent of the total DNA of the cell. Plasmid DNA is usually separable from host cell DNA by virtue of the great difference in size between them. Plasmids can replicate independently of the rate of host cell division and in some cases their replication rate can be controlled by the investigator by variations in the growth conditions. Although the plasmid exists as a closed ring, it is posible by artificial means to introduce a segment of DNA into the plasmid, forming a recombinant plasmid with enlarged molecular size, without substantially affecting its ability to replicate or to express whatever genes it may carry. The plasmid therefore serves as a useful vector for transferring a segment of DNA into a new host cell. Plasmids which are useful for recombinant DNA technology typically contain genes which may be useful for selection purposes, such as genes for drug resistance.

In addition to the specialized techniques of the prior art just described, the present work also entails the use of numerous conventional techniques known in the art including chromatography, electrophoresis, centrifugation, solvent extraction, and precipitation. Reference is made to such specific techniques in the examples.

For general background see Watson, J. D., *The Molecular Biology of the Gene*, 3d Ed., Benjamin, Menlo Park, Calif., (1976); Davidson, J. N., *The Biochemistry of the Nucleic Acids*, 8th Ed., Revised by Adams, R. L. P., Burdon, R. H., Campbell, A. M. and Smellie, R. M. S., Academic Press, New York, (1976); and Hayes, W., "The Genetics of Bacteria and Their Viruses", *Studies in Basic Genetics and Molecular Biology*, 2d Ed., Blackwell Scientific Pub., Oxford (1968).

To illustrate the practice of the present invention, the isolation and transfer of the rat insulin gene is described in detail. Insulin was chosen for this effort because of its central significance from the standpoint of clinical medicine, and from the standpoint of basic research. The disclosed procedure is applicable by those of orindary skill in the art to the isolation of the insulin gene of other organisms, including humans.

Insulin was first isolated in 1922. At the present time, the use of this hormone in the treatment of diabetes is well-known. Although slaughterhouses provide beef and pig pancreases as insulin sources, a shortage of the hormone is developing as the number of diabetics increases worldwide. Moreover, some diabetics develop an allergic reaction to beef and pig insulin, with deleterious effects. The ability to produce human insulin to quantities sufficient to satisfy world needs is therefore highly desirable. Manufacturing human insulin in bacteria is a technique which could achieve this desired goal. However, prior to the present invention, progress toward this desired goal has been thwarted by the fact that no technique has been developed to introduce the insulin gene into a bacteria. The present invention provides such a technique.

Further research is required before it is possible to make proteins, like insulin, on a commercial scale from bacteria which have received a specific DNA sequence that is the genetic determinant of that protein. Whether or not a gene within a cell makes protein depends on many factors, including the position and orientation of the DNA relative to special sequences of the host DNA that tell the host cell when to start and stop making protein. The first steps, isolating the appropriate gene and transferring it to bacteria, are now achievable by the processes of the present invention. These processes are described in detail for the insulin gene.

In addition to its direct usefulness in the production of proteins of therapeutic interest by microorganisms, the process of the present invention in research is designed to gain a further understanding of the expression of insulin genes in normal and pathological states such as diabetes. Little is currently known about the nature of such control. Although insulin is composed of two polypeptide chains, designated A and B, it is the product of a single gene. Insulin is produced specifically by certain endocrine cells, termed B cells, in the pancreas. The B cells are found as part of certain histologically distinct structures within the pancreas known as the islets of Langerhans, where they comprise the majority of cells.

The ability to obtain DNA having a specific sequence which is the genetic code for a specific protein makes it possible to modify the nucleotide sequence by chemical or biological means such that the specific protein ultimately produced is also modified. This would make it possible to produce, for example, a modified insulin tailored to suit a specific medical need. The genetic capacity to produce any insulin-related amino acid sequence having the essential functional properties of insulin may therefore be conferred upon a microorganism.

The ability to transfer the genetic code for a specific protein necessary to the normal metabolism of a particular higher organism to a microorganism such as a bacterium opens significant possibilities for culture production of such proteins. This in turn affords significant possibilities for augmenting or replacing the output of such proteins with those produced by microorganisms altered pursuant to this invention, whenever the ability of the higher organism to function normally in the production of such proteins has been impaired, and suggest, e.g., the possibility of establishing symbiotic relationships between microorganisms produced pursuant to this invention and human beings with chronic or acute deficiency diseases, whereby microorganisms genetically altered as herein taught might be implanted in or otherwise associated with a human to compensate for the pathologic deficiency in the metabolism of the latter.

SUMMARY OF THE INVENTION

A process is disclosed for isolating a specific nucleotide sequence containing genetic information, synthesis of DNA having the specific nucleotide sequence and transfer of the DNA to a host microorganism. While the invention is particularly exemplified by a specific DNA sequence transferred to a bacterium and containing the structural gene for rat preproinsulin, it is contemplated that the method is of good applicability to the transfer of any desired DNA sequence from a higher organism, such as a vertebrate, to any microorganism. A higher organism is here defined as any eucaryotic organism having differentiated tissues, including but not limited to, insects, molluscs, plants, vertebrates including mammals, the latter category including cattle, swine, primates and humans. A microorganism, as is understood in the art, may be any microscopic living organism such as is included in the term, protist, whether procaryotic or eucaryotic, including for example bacteria, protozoa, algae and fungi, the latter category including yeasts. In the process, a selected cell population is first isolated by an improved method. Intact mRNA is extracted from the cells by a novel procedure whereby virtually all RNAse activity is suppressed. Intact messenger RNA is purified from the extract by column chromatography and subjected to the action of the enzyme reverse transcriptase acting in the presence of the four deoxynucleoside triphosphates needed to synthesize a complementary (cDNA) strand. The product of this first reaction with reverse transcriptase is subjected to a procedure which selectively removes the ribonucleotide sequence. The remaining deoxynucleotide sequence, complementary to the original nRNA, is incubated in a second reaction with reverse transcriptase of DNA polymerase in the presence of the four deoxynucleoside triphosphates. The resulting product is a duplex cDNA structure having its comple mentary strands joined together at one end by a single stranded loop. This product is then treated with single strand specific nuclease which cleaves the single stranded loop. The resulting double stranded cDNA is next extended in length by the addition at both ends of a specific DNA containing a restriction enzyme recognition site sequence. The addition is catalyzed by a DNA ligase enzyme. The extended cDNA is next treated with a restriction endonuclease, producing self-complementary single stranded ends at the five-prime termini of each strand in the duplex.

A plasmid DNA having a recognition site for the same restriction endonuclease is treated with the enzyme, in order to cleave the polynucleotide strand and produce self-complementary single strand nucleotide sequences at the 5' termini. The 5' terminal phosphate groups on the single stranded ends are removed to prevent the plasmid from forming a ring structure capable of transforming a host cell. The prepared cDNA and plasmid DNA are incubated together in the presence of DNA ligase. Under the reaction conditions described, the formation of a viable closed ring of plasmid DNA can only occur if a segment of cDNA is included. The plasmid containing the cDNA sequence is then introduced into an appropriate host cell. Cells which have received a viable plasmid are detected by the appearance of colonies having a genetic trait conferred by the plasmid, such as drug resistance. Pure bacterial strains containing the recombinant plasmid having the incorporated cDNA sequence are then grown up, and the recombinant plasmid reisolated. Large amounts of recombinant plasmid DNA may be prepared in this manner and the specific cDNA sequence reisolated therefrom by endonucleolytic cleavage with the appropriate restriction enzyme.

The basic process of the invention is applicable to the isolation and transfer to a host microorganism of any desired nucleotide sequence obtained from a higher organism, including man. It is contemplated that the method will be useful in the transfer of a gene coding for a specific protein which may have medical or industrial value. In demonstrating the invention, the nucleotide sequence coding for insulin has been isolated from rat, transferred to a bacteria and replicated therein. The method is applicable to the transfer of a nucleotide sequence isolated from a human source.

DETAILED DESCRIPTION OF THE INVENTION

The present invention subsumes a method for the isolation of a DNA molecule of specific nucleotide sequence and its transfer to a microorganism, wherein the original nucleotide sequence of the DNA is found after replication in the transferee organism.

The sequence of steps comprising the process of the invention can be classified in four general categories:
1. The isolation of a desired cell population from a higher organism.

There are two potential sources of a genetic sequence coding for specific protein: the DNA of the source organism itself, and an RNA transcript of the DNA. The current safety requirements of the National Institute of Health specify that human genes of any kind can be put into recombinant DNA, and then into bacteria, only after the genes have been very carefully purified or in special high-risk (P4) facilities. See Federal Register, Vol. 41, No. 131, July, 7, 1967, pp. 27902-27943. Therefore, for any procedure having potential utility for the production of the human protein, such as the present process, the preferred approach is the isolation of specific mRNA having a nucleotide sequence which codes for the desired protein. The adoption of this strategy has the further advantage that the mRNA can be more easily purified than DNA extracted from the cell. In particular, it is possible to take advantage of the fact that in highly differentiated organisms such as vertebrates, it may be possible to identify a specific population of cells having a specific location within the organism, whose function is primarily devoted to the production of the protein in question. Alternatively, such a population may exist during a transient developmental stage of the organism. In such cell populations, a large portion of the mRNA isolated from the cells will have the desired nucleotide sequence. Therefore, the choice of cell population to isolate, and the method of isolation employed, can be substantially advantageous from the standpoint of the initial purity of the mRNA isolated therefrom.

The process employed herein is a modification of the procedure of Lacy, P. E., and Kostianovsky, M., *Diabetes* 16, 35 (1967). Details of the present procedure are given in Example 1. The process is applicable, within the scope of ordinary skill in the art, to the isolation of islet cells from human pancreas. Careful attention to exact procedural detail is essential. The most important details include the use of silicone-treated glassware, the use of empirically-selected collagenase, the use of the proper ratio of incubation volume to container size, the use of a proper shaking rate and careful visual observation of the course of collagenase digestion to ensure that the reaction has proceeded to the optimum extent. The process of the present invention has the advantage of improved reproducibility and permits successful isolation of islet cells on a larger scale than heretofore practicable.

Insulin-producing cells may be derived from other sources, such as fetal calf pancreas or cultured islet tumor cells. The isolation of pure islet cells will be much simpler in such cases, especially where pure cell cultures are used. The method of isolating islet cells described supra would not be needed in such cases, however, the method remains advantageous because of its general applicability.

2. Extraction of mRNA.

An important feature of the present invention is the essentially complete removal of RNase activity in the cell extract. The mRNA to be extracted is a single polynucleotide strand, unpaired with any complementary strand. Therefore, the hydrolytic cleavage of a single phosphodiester bond in the sequence would render the entire molecule useless for the purpose of transferring an intact genetic sequence to a microorganism. As stated hereinabove, the enzyme RNase is widely distributed, active and exceptionally stable. It is found on the skin, survives ordinary glassware washing techniques and sometimes contaminates stocks of organic chemicals. The difficulties are especially acute in dealing with extracts of pancreas cells, since the pancreas is a source of digestive enzymes and is, therefore, rich in RNase. However, the problem of RNase contamination is present in all tissues, and the method disclosed herein to eliminate RNase activity is applicable to all tissues. The exceptional effectiveness of the method is demonstrated in the present invention by the successful isolation of intact mRNA from isolated islet cells of the pancreas.

RNase is effectively inhibited during isolation from intact cells by homogenizing a cell preparation in guanidinium thiocyanate buffered to low pH and containing mercaptoethanol. Other guanidinium salts such as guanidinium hydrochloride may be used, but they are less effective denaturing agents. The use of guanidinium hydrochloride has been suggested by Cox, R. A., *Methods in Enzymology* 12, Part B, pp. 120-129 (1968), but the present workers have found this method inadequate for the purpose herein described. Mercaptoethanol further reduces RNase activity by disrupting its intermolecular disulfide bonds. The combination of mercaptoethanol with a patent denaturing agent such as guanidinium thiocyanate, pursuant to this invention, tends to enhance the effectiveness of mercaptoethanol by rendering the inactivation of RNase essentially irreversible. The pH may be varied in the range of 5.0–8.0. The preferred pH is 5.0 because of its effect in inducing a more tightly folded conformation of the RNA, thereby rendering it more resistant to RNase activity.

Following the homogenization step, the RNA is separated from the bulk of the cellular protein and DNA. A variety of procedures has been developed for this purpose, any of which is suitable, all of which are well-known in the art. A common practice in the prior art is to use an ethanol precipitation procedure which selectively precipitates RNA. The preferred technique of the present invention is to bypass the precipitation step and layer the homogenate directly on a solution of 5.7M cesium chloride in a centrifuge tube and then to subject the tube to centrifugation as described in Glisin, V., Crkvenjakov, R., and Byus, C., *Biochemistry* 13, 2633 (1974). This method is preferred because an environment continuously hostile to RNase is maintained and RNA is recovered in high yield, free of DNA and protein.

The above recited procedures result in the purification of total RNA from the cell homogenate. However, only a portion of such RNA is the desired mRNA. In order to further purify the desired mRNA, advantage is taken of the fact that in the cells of higher organisms, mRNA, after transcription, is further processed in the cell by the attachment of polyadenylic acid. Such mRNA containing poly A sequences attached thereto may be selectively isolated by chromatography on columns of cellulose to which is attached oligo-thymidylate, as described by Aviv, H. and Leder, P., supra. The foregoing procedures are sufficient to provide essentially pure, intact, translatable mRNA from sources rich in RNase. The purification of mRNA and subsequent in vitro procedures may be carried out in essentially the same manner for any mRNA, regardless of the source organism.

Under certain circumstances, for example when tissue culture cells are used as the mRNA source, RNase contamination may be sufficiently low that the RNase inhibition method just described will not be needed. In such cases, prior art techniques for reducing RNase activity may be sufficient.

3. Formation of cDNA.

Reference is made to FIG. 1 for a schematic representation of the remaining steps of the process. The first step in this process is the formation of a sequence of DNA complementary to the purified mRNA. The enzyme of choice for this reaction is reverse transcriptase, although is principle any enzyme capable of forming a faithful complementary DNA strand using the mRNA as a template could be used. The reaction may be carried out under conditions described in the prior art, using mRNA as a template and a mixture of four deoxynucleoside triphosphates as precursors for the DNA strand. It is convenient to provide that one of the deoxynucleoside triphosphates be labeled with $^{32}P$ in the alpha position in order to monitor the course of the reaction, provide a tage for recovering the product after separation procedures such as chromatography and electrophoresis, and for the purpose of making quantitive estimates of recovery. See Efstratiadis, A., et al., supra.

As diagrammed in the figure, the product of the reverse transcriptase reaction is a double stranded hairpin structure with non-covalent linkage between the RNA strand and the DNA strand.

The product of the reverse transcriptase reaction is removed from the reaction mixture by standard techniques known in the art. It has been found useful to employ a combination of phenol extraction, chromatography on Sephadex[1] G-100 and ethanol precipitation.

[1]. Trademark, Pharmacia Inc., Uppsala, Sweden.

Once the cDNA has been enzymatically synthesized, the RNA template may be removed. Various procedures are known in the prior art for the selective degradation of RNA in the presence of DNA. The preferred method is alkaline hydrolysis, which is highly selective and can be readily controlled by pH adjustment.

Following the alkaline hydrolysis reaction and subsequent neutralization, the $^{32}P$ labeled cDNA may be concentrated by ethanol precipitation if desired. Synthesis of a double stranded hairpin cDNA is accomplished by the use of an appropriate enzyme, such as DNA polymerase or reverse transcriptase. Reaction conditions similar to those described previously are employed, including the use of an $\alpha$-$^{32}P$ labeled nucleoside triphosphate. Reverse transcriptase is available from a variety of sources. A convenient source is avian myeloblastosis virus. The virus is available from Dr. D. J. Beard, Life Sciences Incorporated, St. Petersburg, Fla., who produces the virus under contract with the National Institutes of Health.

Following the formation of the cDNA hairpin, it may be convenient to purify the DNA from the reaction mixture. As described previously, it has been found convenient to employ the steps of phenol extraction, chromatography on Sephadex G-100 and ethanol precipitation to purify the DNA product free of contaminating protein.

The hairpin structure may be converted to a conventional double stranded DNA structure by the removal of the single stranded loop joining the ends of the complementary strands. A variety of enzymes capable of specific hydrolytic cleavage of single stranded regions of DNA is available for this purpose. A convenient enzyme for this purpose is the S1 nuclease isolated from *Aspergillus oryzae*. The enzyme may be purchased from Miles Research Products, Elkhart, Ind. Treatment of the hairpin DNA structure with S1 nuclease results in a high yield of cDNA molecules with base paired ends. After the extraction, chromatography and ethanol precipitation as previously described. The use of reverse transcriptase and S1 nuclease in the synthesis of double stranded cDNA transcripts of mRNA has been described by Efstratiadis et al., supra.

The next step in the process involves the treatment of the ends of the cDNA product to provide appropriate sequences at each end containing a restriction endonuclease recognition site. The choice of DNA fragment to be added to the ends is determined by matters of manipulative convenience. The sequence which is to be added to the ends is chosen on the basis of the particular restriction endonuclease enzyme chosen, and this choice in turn depends on the choice of DNA vector with the cDNA is to be recombined. The plasmid chosen should have at least one site susceptible to restriction endonuclease cleavage. For example, the plasmid pMB9 contains one restriction site for the enzyme Hind III. Hind III is isolated from *Hemophilus influenzae* and purified by the method of Smith, H. O., and Wilcox, K. W., *J. Mol. Biol*, 51, 379 (1970). The enzyme, Hae III, from *Hemophilus aegypticus* is purified by the method of Middleton, J. H., Edgell, M. H., and Hutchison III, C. A., *J. Virol*, 10, 42 (1972). An enzyme from *Hemophilus suis*, designated Hsu I, catalyzes the same site-specific hydrolysis, at the same recognition site, as Hind III. These two enzymes are therefore considered as functionally interchangeable.

It is convenient to employ a chemically synthesized double stranded decanucleotide containing the recognition sequence for Hind III, for the purpose of attachment to the ends of the cDNA duplex. The double stranded decanucleotide has the sequence shown in FIG. 1. See Heyneker, H. L., et al., and Scheller, R. H., et al., supra. A variety of such synthetic restriction site sequences is available to workers in the art, so that it is possible to prepare the ends of a duplex DNA so as to be sensitive to the action of any of a wide variety of restriction endonucleases.

The attachment of restriction site sequences to the ends of cDNA may be accomplished by any step known to workers in the art. The method of choice is a reaction termed blunt end ligation, catalyzed by DNA ligase purified by the method of Panet, A., et al., *Biochemistry* 12, 5045 (1973). The blunt end ligation reaction has been described by Sgaramella, V., et al., supra. The product of the blunt end ligation reaction between a blunt ended cDNA and a large molar excess of double stranded decanucleotide containing the Hind III endonuclease restriction site is a cDNA having Hind III restriction site sequences at each end. Treatment of the reaction product with Hind III endonuclease results in cleavage at the restriction site with the formation of single stranded 5' self-complementary ends, as shown in FIG. 1.

4. Formation of a recombinant vector.

In principle, a wide variety of viral and plasmid DNA's could be used to form recombinants with a cDNA prepared in the manner just described. The principal requirements are that the DNA be capable of entering a host cell, undergoing replication in the host cell and should, in addition, have a genetic determinant through which it is possible to select those host cells which have received the vector. For reasons of public safety, however, the range of choice should be restricted to those vector species deemed suitable for the type of experiments employed, in according with the NIH guidelines, supra. The list of approved DNA vectors is continuously being enlarged, as new vectors are developed and approved by the NIH Recombinant DNA Safety Committee, and it is to be understood that this invention contemplates the use of any viral and plasmid DNA's that have the described capabilities, including those on which NIH approval may later be granted. Suitable vectors which are currently approved for use include a variety of derivatives of bacteriophage lambda (See e.g. Blattner, F. R., Williams, B. G., Bluckl, A. E., Denniston-Thompson, K., Faber, H. E., Furlong, L. A., Grunwald, D. J., Kiefer, D. O., Moore, D. D., Schumm, J. W., Sheldon, E. L., and Smithies, O., *Science* 196, 161 (1977) and derivatives of the plasmid col El, see e.g. Rodriguez, R. L., Bolivar, S., Goodman, H. M., Boyer, H. W., and Betlach, M. N., ICN-UCLA Symposium on Molecular Mechanisms In The Control of Gene Expression, D. P. Nierlich, W. J. Rutter, C. F. Fox, Eds. (Academic Press, NY, 1976), pp. 471–477. Plasmids derived from col El are characterized by being relatively small, having molecular weights of the order of a few million, and having the property that the number of copies of plasmid DNA per hot cell can be increased from 20–40 under normal conditions to 1000 or more, by treatment of the host cells with chloramphenicol. The ability to amplify the gene dosage within the host cell makes it possible under appropriate circumstances, under the control of the investigator, to cause the host cell to produce primarily proteins coded for by genes carried on the plasmid. Such derivatives of col El are therefore preferred in the process of the present invention. Suitable derivatives of col El include the plasmids pMB-9, carrying the gene for tetracycline resistance, and pBR-313, pBR-315, pBR-316, pBR-317 and pBR-322, which contain, in addition to the tetracycline resistance gene, a gene for ampicillin resistance. The presence of the drug resistance genes provides a convenient way for selecting cells which have been successfully infected by the plasmid, since colonies of such cells will grow in the presence of the drug whereas cells which have not received the plasmid will not grow or form colonies. In the experiments described herein as specific examples of the present invention, a plasmid derived from col El was used throughout, containing, in addition to the described drug resistance marker, one Hind III site.

As with the choice of plasmid, the choice of a suitable host is in principle very broad but for purposes of public safety, narrowly restricted. A strain of *E. Coli* designated X-1776 has been developed and has received NIH approval for processes of the type described herein. See Curtiss, III, R., *Ann. Rev. Microbiol.*, 30, 507 (1976). As in the case of the plasmids, it will be understood that the invention contemplates use of any host cell strains having the capability of acting as a transferee for the chosen vector, including protists other than bacteria, for example yeasts, whenever such strains are approved for use under the NIH guidelines.

Recombinant plasmids are formed by mixing restriction endonuclease-treated plasmid DNA with cDNA containing end groups similarly treated. In order to minimize the chance that segments of cDNA will form combinations with each other, the plasmid DNA is added in molar excess over the cDNA. In prior art procedures this has resulted in the majority of plasmids circularizing without an inserted cDNA fragment. The subsequently transformed cells contained mainly plasmid and not cDNA recombinant plasmids. As a result, the selection process was very tedious and time consuming. The prior art solution to this problem has been to attempt to devise DNA vectors having a restriction endonuclease site in the middle of a suitable marker gene such that the insertion of a recombinant divides the gene thereby causing loss of the function coded by the gene.

Preferably, a method for reducing the number of colonies to be screened for recombinant plasmids is employed. The method involves treating plasmid DNA cut with the restriction endonuclease with alkaline phosphatase, an enzyme commercially available from several sources, such as Worthington Biochemical Corporation, Freehold, N.J. Alkaline phosphatase treatment removes the 5'-terminal phosphates from the endonuclease generated ends of the plasmid and prevents self-ligation of the plasmid DNA. Consequently, circle formation, hence transformation, will be dependent on the insertion of a DNA fragment containing 5'-phosphorylated termini. The described process reduces the relative frequency of transformation in the absence of recombination to less than 1 to $10^{+4}$.

For the purpose of illustrating the above described procedures, cDNA coding for rat insulin has been isolated and recombined with a plasmid. The DNA molecules were used to transform E. COL1 X-1776. Transformants were selected by growth on medium containing tetracycline. One recombinant plasmid DNA obtained from transformed cells was found to contain an inserted DNA fragment approximately 410 nucleotides in length. Other recombinants, isolated by similar procedures, were also obtained and analyzed. The inserted fragments were released from the plasmid by Hind III or HSu I endonuclease digestion and were subjected to DNA sequence analysis by the method of Maxam, A. M. and Gilbert, W., *Proc. Natl. Acad. Sci. USA* 74, 560 (1977). The nucleotide sequences of the inserted DNA fragments were found to be overlapping and to contain the entire coding region for rat proinsulin I, as well as 13 out of 23 amino acids of the prepeptide sequence. A composite of the nucleotide sequence of this region was constructed as shown hereinafter.

The process just described is generally applicable to the isolation and purification of a gene from a higher organism, including a human gene, and its transfer to and replication in a microorganism. Novel recombinant plasmids containing all or a portion of the isolated gene are described. Novel microorganisms hitherto unknown in nature are described, having as part of their genetic makeup a gene from a higher organism. Specific examples detailing each step of the process as applied to the isolation, purification and transfer of the rat insulin gene into *E. coli* will next be described, in order to more clearly reveal time characteristics and utility of the invention. The following examples characterise recombinant plasmids containing portions of the rat insulin gene, and novel microorganisms containing portions of the rat insulin gene.

EXAMPLE 1

The described procedures demonstrate the extraction and isolation of rat insulin mRNA, the synthesis of a DNA complementary thereto and the characterization of the complementary DNA. To prepare purified rat islet cells, the pancreas of an anesthetized rat was infused with Hank's salt solution by retrograde infusion into the pancreatic duct. Hank's salt solution is a standard salt solution mixture known in the art and available from a number of commercial sources, such as Grand Island Biological Supply Company, Grand Island, N.Y. The pancreas was then removed, minced in Hank's solution at 0° C. and digested with collagenase and soybean trypsin inhibitor. All procedures were conducted at 0° C.–4° C. unless otherwise specified. The conditions of the digestion procedure were extremely critical. Two minced rat pancreases in an 8 ml total volume in Hank's medium were placed in a 30 ml glass tube. All glass tubes were pretreated with silicone[2]. The incubation mixture contained 12 mg collagenase, an enzyme prepared from *Clostridium histolyticum*, essentially by the method of Mandl, I., Mackennan, J. D. and Howes, E. L., *J. Clin. Invest.* 32, 1323 (1943), type CLS IV, obtained from Worthington Biochemical Corporation, Freehold, N.J., and 1 mg soybean trypsin inhibitor obtained from Sigma Chemical Company, St. Louis, Mo. Incubation was carried out at 37° C. for 25 minutes with shaking at the rate of 90 strokes per minute. Continuous inspection was required to insure that the collagenase digestion had proceeded to an optimal extent. If the incubation was too short, the islet cells were incompletely released and if the incubation too long the islet cells would begin to lyse. Following incubation the tube was centrifuged for 1 minute at 200×G. The supernatant was decanted and the pellet washed with Hank's solution, and this procedure was repeated five times. After the final centrifugation, the pellet was suspended in 15 ml. Ficoll[3], having a density of 1.085. A layer of 8 ml. Ficoll of density 1.080 was added, a layer of 5 ml. Ficoll of density 1.060 was added, and the tube was centrifuged in a swinging bucket rotor for 5 minutes at 500×G followed by 5 minutes at 2000×G. As a result of the foregoing process, acinar cells remained at the bottom of the tube and islet cells rose in the gradient and formed a band between the two top layers. The islet cell band contained contaminating gaglion cells, lymph nodes, and connective tissue. Large contaminating fragments were removed from the material in the band. The remainder of the preparation was placed under a dissecting microscope where visible contaminating materials were removed by hand using a micropipette. The cell preparation was then diluted in Hank's solution and centrifuged. The supernatant was decanted and the cell pellet stored frozen in liquid nitrogen.

2. Siliclad, trademark, Clay-Adams Division, Becton-Dickinson Inc., Parsippany, N.J.,
3. Trademark, Pharmacia Chemical Company, Uppsala, Sweden.

Islet cells pooled from 200 rats were homogenized in 4M guanidinium thiocyanate[4] containing 1M β-mercaptoethanol buffered to pH 5.0 at 4° C. The homogenate was layered over 1.2 ml, 5.7M CsCl containing 100 mM EDTA and centrifuged for 18 hours at 37,000 rpm in the SW 50.1 rotor of a Beckman Ultracentrifuge at 15° C. (Beckman Instrument Company, Fullerton, Calif.). RNA traveled to the bottom of the tube.

4. Tridom, trademark, Fluka AG Chemische Fabrik, Buchs, Switzerland.

Polyadenylated RNA was isolated by chromatography of the total RNA preparation on oligo(dT)-cellulose according to the procedure of Aviv, H., and Leder, P., supra.

Avian myeloblastosis virus reverse transcriptase, provided by D. J. Beard, Life Science Inc., St. Petersburg, Fla., was used to transcribe total polyadenylated RNA from rat isolets of Langerhans into cDNA. The reactions were carried out in 50 mM Tris-HCl, pH 8.3, 9 mM MgCl$_2$, 30 mM NaCl, 20 mM beta-mercaptoethanol, 1 mM each of 3 nonradioactive deoxyribonucleoside triphosphates, 250 μM of the fourth deoxynucleoside triphosphate labeled with α-$^{32}$P, specific activity 50–200 curies per mole, 20 μg/ml oligo-dT$_{12-18}$ from Collaborative Research, Waltham, Mass., 100 μg/ml polyedenylated RNA and 200 units/ml reverse transcriptase. The mixture was incubated at 45° C. for fifteen minutes. After addition of EDTA-Na$_2$ to 25 mM, the solution was extracted with an equal volume of water-saturated phenol, followed by chromatography of the aqueous phase on a Sephadex G-100 column, 0.3 cm in diameter by 10 cm in height, in 10 mM Tris-HCl, pH 9.0, 100 mM NaCl, 2 mM EDTA. Nucleic acid eluted in the void volume was precipitated with ethanol after addition of ammonium acetate, pH 6.0, to 0.25M. The precipitate was collected by centrifugation, the pellet was dissolved in 50 μl of freshly prepared 0.1M NaOH and incubated at 70° C. for 20 minutes to hydrolyze the RNA. The mixture was neutralized by the addition of 1M sodium acetate, pH 4.5, and the $^{32}$P-cDNA product was precipitated with ethanol and redissolved in water. Aliquots of single stranded cDNA were analyzed on native polyacrylamide gels by the method of Dingman, C. W., and Peacock, A. C., *Biochemistry* 7, 659 (1968). The gels were dried and the $^{32}$P DNA detected by autoradiography using Kodak No- Screen NS-2T[5] film. The cDNA was heterodisperse, as judged by the electrophoresis pattern. It contained at least one prominent cDNA species of about 450 nucleotides, as judged by comparison with known standards.

5. Trademark, Eastman Kodak Corporation, Rochester, N.Y.

EXAMPLE 2

The synthesis and characterization of double standard cDNA containing the sequence of rat insulin is described. The single stranded cDNA product of Example 1 was treated with reverse transcriptase to synthesize the complementary strand. Reaction mixture contained 50 mM Tris-HCL, pH 8.3, 9 mM $MgCl_2$, 10 mM dithiothreitol, 50 mM each of three unlabeled deoxyribonucleoside triphosphates, 1 mM of an alpha-$^{32}$-P-labeled nucleoside triphosphate of specific activity 1–10 curies per millimole, 50 µg/ml cDNA and 220 units/ml of reverse transcriptase. The reaction mixture was incubated at 45° C. for 120 minutes. The reaction was stopped by addition of EDTA-$Na_2$ to 25 mM, extended with phenol and chromatographed on Sephadex G-100 followed by ethanol precipitation. An aliquot of the reaction product having 500 cpm to 1,000 cpm was analyzed by gel electrophoresis as described in Example 1. A heterodisperse band centering around 450 nucleotides in length was observed, as determined by comparison with standard samples. Aliquots of the DNA reaction products of Example 1 and Example 2 were separately treated by digestion with an excess of restriction endonuclease Hae III and similarly analyzed by gel electrophoresis. Both the products were cleaved by the endonuclease so that two bands of radioactivity were observed on gel electrophoresis. The bands resulting from the cleavage of double stranded cDNA represented essentially the same length cleavage products as did those resulting from the cleavage of the single stranded cDNA.

EXAMPLE 3

The blunt-end ligation of Hind III decanucleotide linkers to rat islet double stranded cDNA of Example 2 is described. The double stranded reaction product of Example 2 at a concentration of 2–5 µg/ml was treated with 30 units of S1 nuclease having an activity of 1200 units/ml, obtained from Miles Laboratories, Elkhart, Ind., in 0.03M sodium acetate, pH 4.6, 0.3M sodium chloride, 4.5 mM $ZnCl_2$ at 22° C. for 30 minutes incubation followed by an additional 15 minutes incubation at 10° C. Addition of Tris-base to 0.1M final concentration, EDTA to 25 mM, and *E. Coli* tRNA, prepared by the method of von Ehrenstein, G., *Methods in Enzymology*, S. P. Colowick and N. O. Kaplan, Eds., Vol. 12A, p. 588 (1967), to 40 µg/ml was used to stop the digestion. After phenol extraction of the reaction mixture and Sephadex G-100 chromatography, the $^{32}$-P-cDNA eluted in the void volume was precipitated with ethanol. This treatment resulted in a high yield of cDNA molecules with base-paired ends necessary for the blunt-end ligation to chemically synthesized decanucleotides. Hind III decamers were prepared by the method of Scheller, R. H., Dickerson, R. E., Boyer, H. W. Rigss, A. D. and Itakura, K., *Science* 196, 177 (1977). Ligation of Hind III decamers to cDNA was carried out by incubation at 14° C. in 66 mM Tris-HCl, pH 7.6, 6.6 mM $MgCl_2$, 1 mM ATP, 10 mM dithiothreitol, 3 mM Hind III decamers having $10^5$ cpm/pmol and T4 DNA ligase, approximately 500 units/ml, for one hour. The reaction mixture was then heated to 65° C. for 5 minutes to inactivate the ligase. KCl to 50 mM final concentration, beta-mercaptoethanol to 1 mM final concentration, and EDTA to 0.1 mM final concentration were added prior to digestion with 150 units/ml Hsu I or Hind III endonuclease for 2 hours at 37° C., Hind III and Hae III endonuclease are commercially available from New England Bio-Labs, Beverly, Mass. The reaction product was analyzed by gel electrophoresis as in Example 1 and a peak corresponding to a sequence of approximately 450 nucleotides was observed, in addition to fragments of cleaved Hind III decamers.

EXAMPLE 4

The formation of a recombinant plasmid and its characterization after replication is described. Plasmid pMB-9 DNA, prepared as described by Rodriguez, R. L., Boliver, F., Goodman, H. M., Boyer, H. W., and Betlach, M., in ICN-UCLA Symposium on Molecular and Cellular Biology, D. P. Wierlich, W. J. Rutter, and C. F. Fox, Eds., (Academic Press, New York 1976) pp. 471–477, was cleaved at the Hind III restriction site with Hsu I endonuclease, then treated with alkaline phosphatase, type BAPF, Worthington Biochemical Corporation, Freehold, N.J. The enzyme was present in the reaction mixture as the level of 0.1 unit/microgram DNA and the reaction mixture was incubated in 25 mM Tris-HCl, for pH 8 for 30 minutes at 65° C., followed by phenol extraction to remove the phosphatase. After ethanol precipitation, the phosphatase treated plasmid DNA was added to cDNA containing Hind III cohesive termini at a molar ratio of 3 moles plasmid to 1 mole cDNA. The mixture was incubated in 66 mM Tris, pH 7.6, 6.6 mM $MgCl_2$, 10 mM dithiothreitol, and 1 mM ATP for one hour at 14° C. in the presence of 50 units/ml of T4 DNA ligase.

The ligation mixture was added directly to a suspension of *E. Coli* X-1776 cells prepared for transformation as follows: Cells were grown to a cell density of about $2 \times 10^8$ cells/ml in 50 ml of medium containing Tryptone 10 g/l, yeast extract 5 g/l, NaCl 10 g/l, NaOH 2 mM, diaminopimelic acid 100 µg/ml and thymine 40 µg/ml, at 37° C. Cells were harvested by centrifugation for 5 minutes at 5,000×G at 5° C., resuspended in 20 ml cold NaCl 10 mM, centrifuged as before and resuspended in 20 ml transformation buffer containing 75 mM $CaCl_2$, 140 mM NaCl and 10 mM Tris pH 7.5, and allowed to remain 5 minutes in ice. The cells were then centrifuged and resuspended in 0.5 ml transformation buffer. Transformation was carried out by mixing 100 µl of the cell suspension with 50 µl recombinant DNA (1 µg/ml). The mixture was incubated at 0° C. for 15 minutes, then transferred to 25° C. for 4 minutes, then at 0° C. for 30 minutes. The cells were then transferred to agar plates for growth under selection conditions.

Screening for recombinant plasmids was carried out at 5 micrograms/ml tetracycline for transformation into the Hind III site. A selected recombinant, designated pAU-1, was isolated. Crude plasmid preparations of 2 µg–5 µg DNA isolated from pAU-1 were digested with an excess of Hsu I endonuclease. EDTA-$NA_2$ 10 mM, and sucrose 10% w/v (i.e., weight to volume), final concentration were then added and the mixture resolved on an 8% polyacrylamide gel. The DNA was found at a position corresponding to about 410 base pairs in length. In a similar experiment, plasmid pBr 322 was employed as the transfer vector. All conditions were as described except final selection of recombinant clones was carried out on plates containing 20 μg/ml ampicillin.

EXAMPLE 5

The DNA from pAU-1 as described in Example 4 was further purified by electrophoresis on a 6% polyacrylamide gel. After elution from the gel the DNA was labeled by incubation with γ-$^{32}$P-ATP and the enzyme polynucleotide kinase under conditions described by Maxam and Gilbert, supra. The enzyme catalyzes the transfer of a radiactive phosphate group from γ-$^{32}$P-ATP to the 5'-ends of the DNA. The enzyme was obtained from *E. coli* by the method of Panet, A., et al., *Biochemistry* 12, 5045 (1973). The DNA thus labeled was cleaved with Hae III endonuclease as described in Example 2, and the two labeled fragments, about 265 and 135 base pairs respectively, were separated on a polyacrylamide gel under the conditions described in Example 1. The isolated fragments were subjected to specific cleavage reactions and sequence analysis according to the method of Maxam and Gilbert, supra. The sequence below is based upon a composite of the findings from this series of experiments and those of a similar series of cDNA using plasmid vectors derived from col E1 such as pMB9 and pBR322. In the sequence of the 5' end, a sequence estimated between 50–120 nucleotides in length is undetermined and the poly dA segment at the 3'-end is of varying length. This sequence is provided as representing the best information presently available, with the understanding that ongoing studies may reveal additional details or may indicate a need for slight revision in some areas. The corresponding amino acid sequence of rat proinsulin I begins at the triplet position marked 1 and ends at triplet position marked 86. Some uncertainty remains with respect to the sequence underlined with a dashed line.

The known amino acid sequence of the human insulin B chain is:

```
1                                         10
Phe—Val—Asn—Glu—His—Leu—Cys—Gly—Ser—His—
                                          20
—Leu—Val—Glu—Ala—Leu—Tyr—Leu—Val—Cys—Gly—
                                          30
—Glu—Arg—Gly—Phe—Phe—Tyr—Thr—Pro—Lys—Thr
```

The amino acid sequences are numbered from the end having a free amino group. See Smith, L. F., *Diabetes* 21 (suppl. 2), 458 (1972).

GENERAL CONCLUDING REMARKS

With the process of the present invention it has become possible for the first time to isolate a nucleotide sequence coding for a specific regulatory protein from a higher organism such as a vertebrate, and transfer the genetic information contained therein to a microorganism where it may be replicated indefinitely. The disclosed process may be applied to the isolation and purification of the human insulin gene, and to its transfer to a microorganism. A novel recombinant plasmid is disclosed, containing within its nucleotide sequence a subsequence having the structure of and transcribed from a gene of a higher organism. A novel microorganism is disclosed, modified to contain a nucleotide sequence having the structure of and transcribed from a gene of a higher organism. The practice of the invention has been illustrated by demonstrating the transfer of the rat gene for the proinsulin I to a strain of *Escherichia coli*. The sequence of the main portion of the transferred gene has been determined and has been found to contain the entire amino acid sequence of rat proinsulin I, as deter-

```
                                                                   1
[undetermined] -----GCC CTG CTC GTC CTC TGG GAG CCC AAG CCT GCT CAG GCT TTT GTC AAA CAG CAC CTT TGT
               10                                    20
GGT CCT CAC CTG GTG GAG GCT CTG TAC CTG GTG TGT GGG GAA CGT GGT TTC TTC TAC ACA CCC AAC
30                                    40                                    . 50
TCC CGT CGT GAA GTG GAG GAC CCG CAA GTG CCA CAA CTG GAG CTG GCT GGA GGC CCG GAG GCC GGG
                                      60                                    70
GAT CTT CAG ACC TGG GCA CTG GAG GTT GCC CGG CAG AAG CGT GGC ATT GTG GAT CAG TGC TGC ACC
80                                    86
AGC ATC TGC TCC CTC TAC CAA CTG CAG AAC TAC TGC AAC TGA
GTTCAATCAATTCCCGATCCACCCCTCTGCAATGAATAAAGCCTTTGAATGAGC-poly A
Scored Sections = Areas of Present Uncertainty
```

EXAMPLE 6

A nucleotide sequence coding for human insulin is isolated, purified and incorporated in a plasmid essentially as described in Examples 1–4, starting from human pancreas tissue isolated from a suitable human source such as a donated pancreas or a fresh cadaver or a human insulinoma. A microorganism is produced, essentially as described in Example 4, having a nucleotide sequence coding for the human insulin A chain and B chain. The known amino acid sequence of human insulin A chain is:

```
1                                  10
Gly—Ile—Val—Glu—Gln—Cys—Cys—Thr—Ser—Ile—

—Cys—Ser—Leu—Tyr—Glu—Leu—Glu—Asn—
                                   20
                        —Tyr—Cys—Asn
``` mined by reference to the known genetic code which is common to all forms of life.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains or which would be readily apparent to those skilled in said art. With that understanding, the invention is not to be limited except to the extent required by the appended claims.

What is claimed is:

1. A recombinant plasmid replicable in procaryotic host containing within its nucleotide sequence a subsequence having the structure of the reverse transcript of an mRNA of a vertebrate, which mRNA encodes insulin.

2. A recombinant procaryotic microorganism modified to contain a nucleotide sequence having the structure of the reverse transcript of an mRNA of a vertebrate, which mRNA encodes insulin.

3. The bacterium *Escherichia coli* which has been modified to contain a nucleotide sequence having the structure of and transcribed from the rat gene for insulin.

4. A microorganism according to claim 2 wherein the vertebrate is a mammal.

5. A microorganism according to claim 2 wherein the vertebrate is a human.

6. A plasmid according to claim 1 comprising a plasmid containing at least one genetic determinant of col E1.

7. A microorganism according to claim 2 comprising a strain of *Escherichia coli*.

* * * * *